(12) United States Patent
Liska

(10) Patent No.: US 7,083,598 B2
(45) Date of Patent: Aug. 1, 2006

(54) TRANSCUTAN CATHETER ASSEMBLY

(76) Inventor: Jan Liska, Sibyllegatan 53, S-114 43, Stockholm (SE)

( * ) Notice: Subject to any disclaimer, the term of this patent is extended or adjusted under 35 U.S.C. 154(b) by 583 days.

(21) Appl. No.: 10/228,223

(22) Filed: Aug. 27, 2002

(65) Prior Publication Data
US 2004/0044314 A1    Mar. 4, 2004

(51) Int. Cl.
*A61M 5/32* (2006.01)
(52) U.S. Cl. .................. 604/180; 604/158; 604/174; 128/DIG. 26
(58) Field of Classification Search ............ 604/158, 604/174, 177, 180, 165.03; 128/DIG. 6, 128/DIG. 26
See application file for complete search history.

(56) References Cited

U.S. PATENT DOCUMENTS

| 3,683,911 A | 8/1972 | McCormich |
| 3,856,020 A | 12/1974 | Kovac |
| 4,698,057 A | 10/1987 | Joishy |
| 4,915,694 A | 4/1990 | Yamamoto et al. |
| 5,356,389 A | 10/1994 | Willing |
| 6,428,516 B1 * | 8/2002 | Bierman ............... 604/174 |
| 2002/0161332 A1 * | 10/2002 | Ramey ............ 604/164.07 |
| 2004/0199122 A1 * | 10/2004 | Bierman et al. ......... 604/174 |

FOREIGN PATENT DOCUMENTS

| EP | 0 396 497 A1 | 4/1990 |
| GB | 1465682 | 2/1977 |
| WO | 80/01458 | 7/1980 |
| WO | 0 497 608 A1 | 8/1992 |
| WO | 0 780 138 A1 | 6/1997 |

* cited by examiner

*Primary Examiner*—Cris Rodriguez
(74) *Attorney, Agent, or Firm*—Birch, Stewart, Kolasch & Birch, LLP

(57) ABSTRACT

A transcutan catheter assembly including a catheter having a distal end and a proximal end, and a collar of a relatively flexible material having an upper surface and a lower surface. The catheter extends in a fluid tight manner through the collar such that the distal end of the catheter protrudes underneath the lower surface of the collar and its proximal end is accessible at the upper surface for the connection of tubing to the catheter. The lower surface of the collar has adhesive properties for fluid tight attachment to the skin of a patient.

8 Claims, 3 Drawing Sheets

TRANSCUTAN CATHETER ASSEMBLY

FIELD OF THE INVENTION

The present invention concerns a transcutan catheter assembly including a catheter associated with means for preventing contamination of the insertion site of the catheter into a patient. It also concerns means for stabilizing the catheter in relation to a patient's skin.

BACKGROUND OF THE INVENTION

Peripheral and central venous catheters are increasingly used in clinical practice. However, complications such as local or systemic infections are frequent for both temporary and indwelling vascular catheters. Annually, in the United States of America there are more than 200,000 cases of nosocomial bloodstream infections, of which 90% are related to the use of an intravascular device. These infections are associated with increased morbidity and mortality, prolonged hospitalization and increasing medical costs.

The method of choice when applying an intravascular catheter is first to insert the catheter, and secondly to fix it to the skin by a surgical plaster, possibly followed by draping the insertion site with a transparent adhesive-covered sheet. The most common underlying pathophysiology for the development of infection is the motion of the catheter at the skin insertion site and external contamination of the insertion site due to lack of protection and sterility around the insertion site.

Several devices and methods have been suggested to overcome one or more of these problems, such as those disclosed in GB 1,465,682, WO 80/01458, U.S. Pat. No. 4,698,057 and EP 0 396 497.

GB 1,465,682 describes a cannula fitted close to its rear, or, proximal end with laterally extending wings that are foldable together to form a handle used when inserting the cannula in a patient. Fixed to the wings is one edge of a flexible sheet carrying a layer of pressure-sensitive adhesive covered by a removable barrier sheet. The flexible sheet extends in a direction away from the direction of insertion of the cannula. The adhesive and its barrier sheet are initially facing upwards. Upon insertion of the cannula, the barrier sheet is removed, and the flexible sheet is folded forwardly over on itself to adhere to the wings and to the skin of the patient not only to the rear and to the sides of the wings as well as to exposed portions of the cannula to keep the latter stabilized, but also beyond the wings to cover the point of insertion of the cannula into the skin of the patient. Thus, the device as a whole is attached to the patient, and the wound is covered which is said to protect it from risk of contact or infection. However, since the flexible sheet is connected to the wings by means of two tongues extending from the flexible sheet and serving as hinges during the folding, the areas underneath each such tongue will not adhere to the skin, thus leaving open entries to the insertion site. Furthermore, the flexible tubing leading to the cannula enters the sealed area underneath the flexible sheet adhering to the skin, and this involves a further risk that bacteria may spread along the tubing along its contact with the skin.

WO 80/01458 discloses a stabilizing fitting for an intravenous catheter comprising a flexible base member having on an upper side a cradle adapted to retain a catheter hub, and on a lower surface a pressure-sensitive adhesive covered by a strippable cover sheet. After the catheter has been inserted and brought into a proper position, its hub is press-fitted into the cradle. Then the cover sheet is stripped from the underside of the fitting and the fitting is dabbed onto the patient's skin to stabilize the catheter. This, however, is only a temporary stabilizing, and the fitting is further stabilized by adhesive tapes passing over wings of the fitting. Apart from this evident drawback, there is no teaching as how to possibly avoid contamination of the insertion site. On the contrary, a conventional plaster is shown to cover the insertion site and the forward, or, distal end of the catheter.

U.S. Pat. No. 4,698,057 discloses an assembly for stabilizing and securing an intravascular needle or catheter like device having wings on each side thereof. Each wing has an adhesive tape roll fixed to it. The wings have suction cups on their undersurfaces that cling to the skin of a patient to stabilize the wings and the catheter while adhesive tape is uncoiled from the tape rolls to permanently secure the assembly to the patient. Even if this complicated device may hold the needle satisfactory relative to the skin of a patient, there is no teaching how to prevent contamination of the insertion site.

EP 0 396 497 discloses a hollow cup-shaped cover for protecting an infusion needle disposed through a body portion and into a vein of a patient. The cover has a planar bottom flange that is to be tightly mounted against the skin of a patient, e.g. by means of an adhesive so as to prevent water and other contaminating and infecting matter from contacting the zone of a body portion where a catheter or the like enters the body portion. The wall of the cover is transparent for visual inspection therethrough. In one embodiment, a tube connected to the proximal end of the catheter extends through an aperture in a wall of the cover, and, in another embodiment, a similar tube extends through an arcuate elevated portion of the bottom flange. This device is a complementary device to an intravascular catheter, i.e., it is not integrated with the catheter itself, it is complicated to apply and, thus, does not lend itself to everyday, routine use.

Non of these prior art devices complies with the need to primarily provide a reliable seal all around an insertion site of a catheter, and secondly to provide stabilization of a catheter or a similar tubular means introduced into the body of a patient.

It is a primary object of the present invention, thus, to provide a device which is simple to apply with a secure fixation and with a complete integration of the skin and the catheter at the insertion site, thereby minimizing the risk of nosocomial infections. A secondary object of the present invention is to integrate, in the device, a stabilizing means providing a secure and reliable holding of the catheter in relation to a patient's skin.

SUMMARY OF THE INVENTION

According to the present invention there is provided a catheter assembly including a catheter and a collar of a relatively flexible material. A lower surface of the collar has adhesive properties so as to enable fluid tight attachment of the collar to a patient's skin. The catheter extends in a fluid tight manner through the collar such that a distal end of the catheter protrudes underneath its lower surface and such that a proximal end of the catheter is accessible at its upper surface for connection of relevant tubing to the catheter.

BRIEF DESCRIPTION OF THE DRAWINGS

Embodiments of the present invention will now be described, reference being made to the accompanying drawings, wherein.

Further scope of applicability of the present invention will become apparent from the detailed description given hereinafter. However, it should be understood that the detailed description and specific examples, while indicating preferred embodiments of the invention, are given by way of example only, since various changes and modifications within the spirit and scope of the invention will become apparent to those skilled in the art from this detailed description.

DETAILED DESCRIPTION OF PREFERRED EMBODIMENTS

Figure 1:
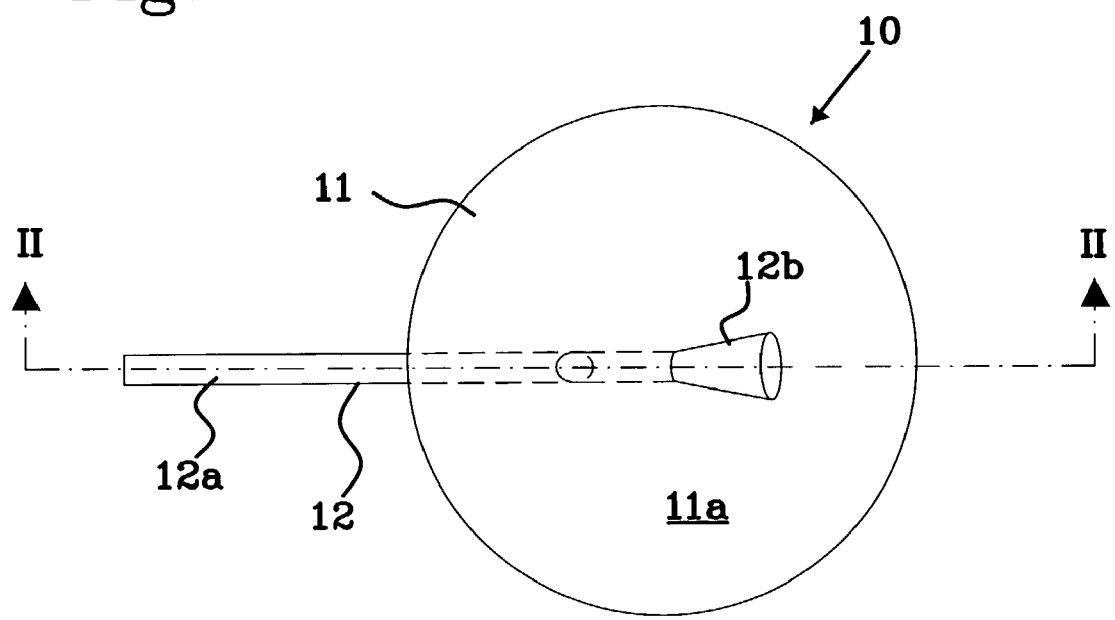
FIG. 1 is a plan view of the device in its basic form.
Figure 2:
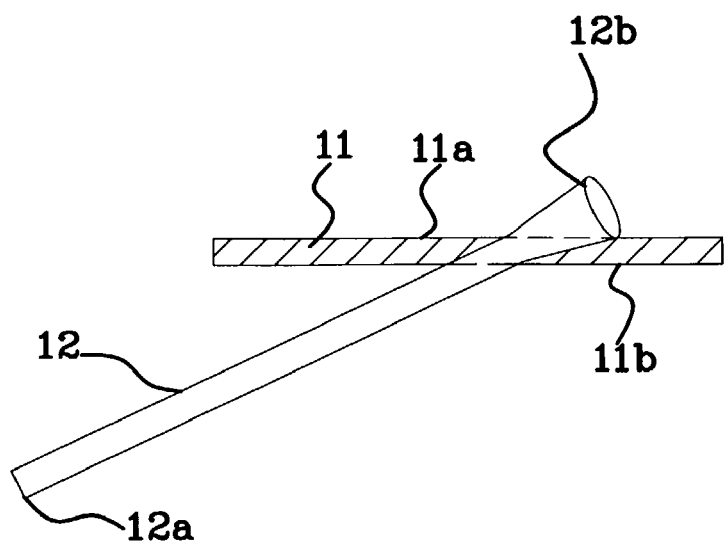
FIG. 2 is a cross section through the device of FIG. 1 taken along line II—II in FIG. 1.

FIGS. 1 and 2 illustrate the inventive idea by showing the simplest conceivable form of device 10 embodying the present invention. It is to be noted, that the relative dimensions of the various items shown are for illustrative purposes only. It includes a collar 11 of a fluid tight, relatively flexible material and a catheter 12. The collar has an upper surface 11a and a lower surface 11b. The collar may have any suitable configuration, such as the substantially circular shape shown. The catheter extends in a fluid tight manner through the collar such that a forward, or, distal end 12a of the catheter extends downwardly and forwardly from the lower surface 11b of the collar and such that a rear, or, proximal end 12b of the catheter is accessible at or above the upper surface 11a of the catheter for connection of suitable tubing (not shown) to the proximal end of the catheter. The lower surface 11b of the collar is adhesive per se or coated by an adhesive layer (not shown) in a manner enabling fluid tight attachment of the sheet to the skin of a patient, thereby effectively preventing access of bacteria, moisture etc. from the circumferential edges of the collar towards its central region, where, in operation of the device, the catheter enters the body of a patient.

Preferred embodiments of the present invention are shown in FIGS. 3–6.

Figure 3:
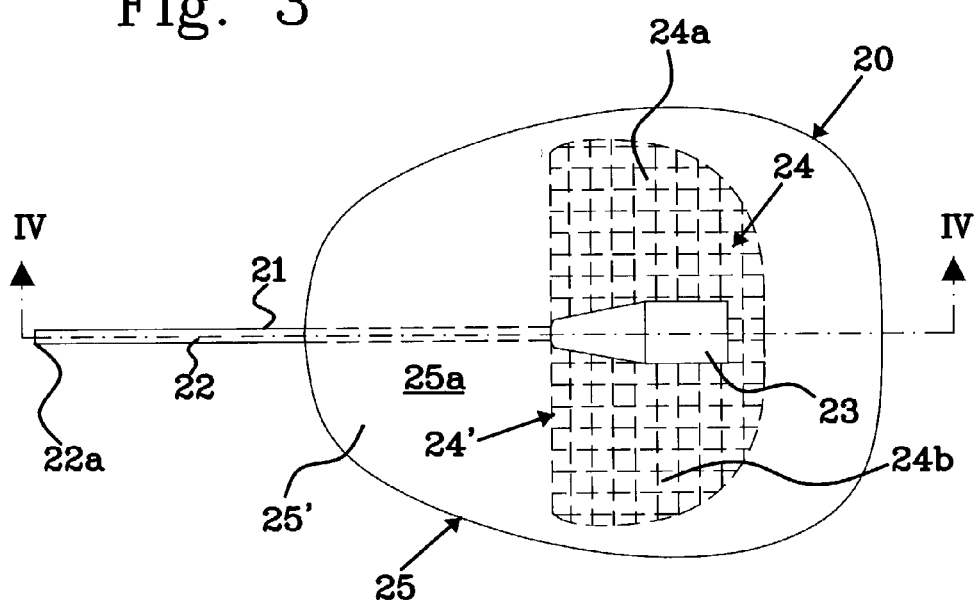
FIG. 3 is a plan view of a preferred embodiment of the invention.

In the plan view of FIG. 3 showing a complete device 20 according to the present invention is partly seen a catheter 21 having a tubular catheter body 22 having a distal end 22a and a proximal end 22b. A hub portion 23 having a longitudinal axis 23' coinciding with the longitudinal axis of the catheter in the normal, straight shape of the latter, is provided at the proximal end 22b. The hub portion may be integrally formed with the catheter body 22, or made separately and tightly connected thereto.

The catheter is shown to be of the blunt-end type necessitating a needle introduced through the catheter from its proximal end to pierce the skin and possibly also a vessel of a patient before it is withdrawn and suitable tubing is connected to the hub portion 23. Evidently, the catheter itself could be of the needle type having a sharpened distal end, or of any other common type.

The hub portion 23 is shown to be formed integrally with a wing-like reinforcement structure 24 including a left wing portion 24a and a right wing portion 24b, and preferably having a net-like design. Alternatively, the hub portion and the reinforcement structure may be formed separately and later joined to enable force transmission between them. The wings 24a, 24b are located in a common plane defining an angle with the axis 23' of the hub portion 23.

A collar member 25 having an upper surface 25a and a lower surface 25b and being formed from a relatively flexible material embeds parts of the unit comprising the catheter 21, the hub portion 23 and the reinforcement structure 24. More precisely, the collar material completely embeds the reinforcement structure 24, whereas a major portion of the catheter body 22 including its distal end 22a extends below the lower surface 25b. The proximal end 22b of the catheter body is held in the hub portion 23 in any suitable and known manner such that fluid communication may be established between the interior of the catheter and the interior of the hub portion, and thereby a proper tubing connected to the hub portion for the supply or discharge of fluid. As an alternative, the hub portion may be associated with the catheter body and connected in any suitable manner to the reinforcement structure, such as by being held in a snap mount integral with the reinforcement structure such as the cradle disclosed in WO 80/01458 initially referred to.

Figure 4:
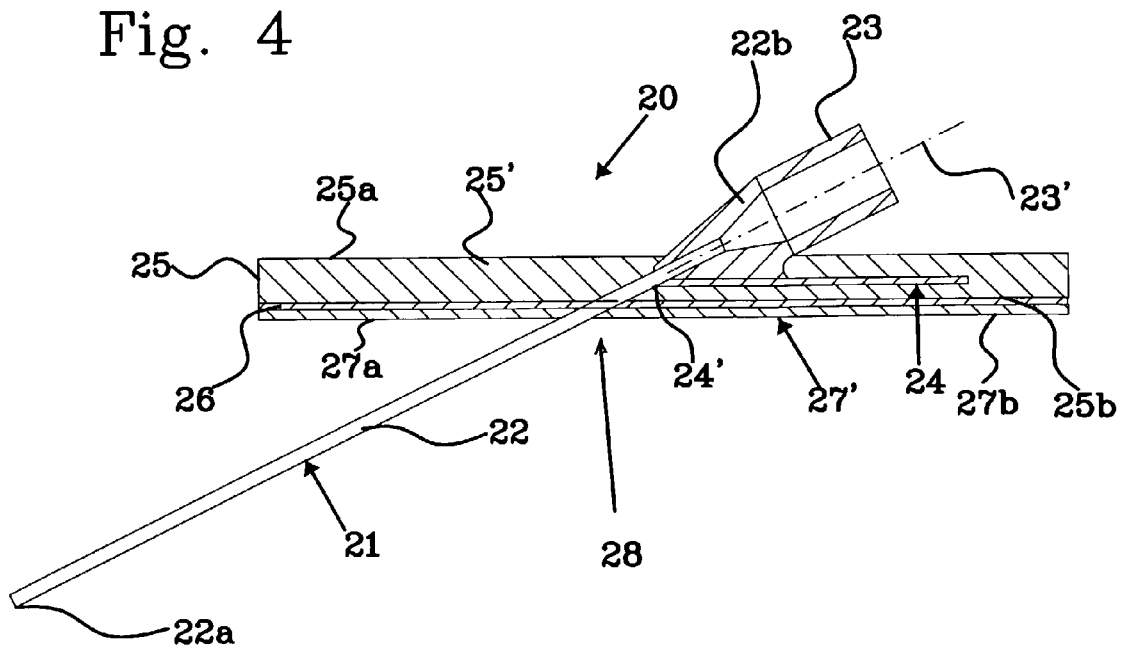
FIG. 4 is a cross section at a somewhat enlarged scale through the device of FIG. 3 taken along line III—III in FIG. 3.

As seen in FIGS. 3 and 4, the wing portions 24a, 24b extend well beyond the end of the hub portion 23 so as to provide a stable holding of the hub portion, and thereby of the proximal end of the catheter held by it, in relation to the collar embedding the wing portions.

The lower surface 25b of the collar is either adhesive per se, or is it coated with an adhesive layer 26 which is covered by a protective sheet 27'.

As seen in FIG. 3, the reinforcement structure, and more precisely its wing portions 24a, 24b, terminates in a forward direction with a straight edge 24' which is substantially perpendicular to the longitudinal axis of the catheter. This straight edge is located in the vicinity of the region where the catheter penetrates the collar. The edge 24' defines a folding line about which a forward portion 25' of the collar may be folded in an upward direction. This is advantageous, since it allows unhindered watch of the insertion site during the insertion of the catheter until the outside of the fold (i.e. the protective sheet 27) abuts the skin surface in the area of the insertion site. Furthermore, the almost double folded collar serves as a grip or handle for holding the assembly during insertion of the catheter. Still further, the hub portion 23 is protected by the forward portion 25' of the collar folded back over it.

The collar can be made of any material suitably flexible to adapt itself to normal curvature of the body surface of a patient. Different thermoplastic, moldable materials may be considered, and the use of a hydrocolloid is also contemplated due to its favourable properties.

Figure 6:
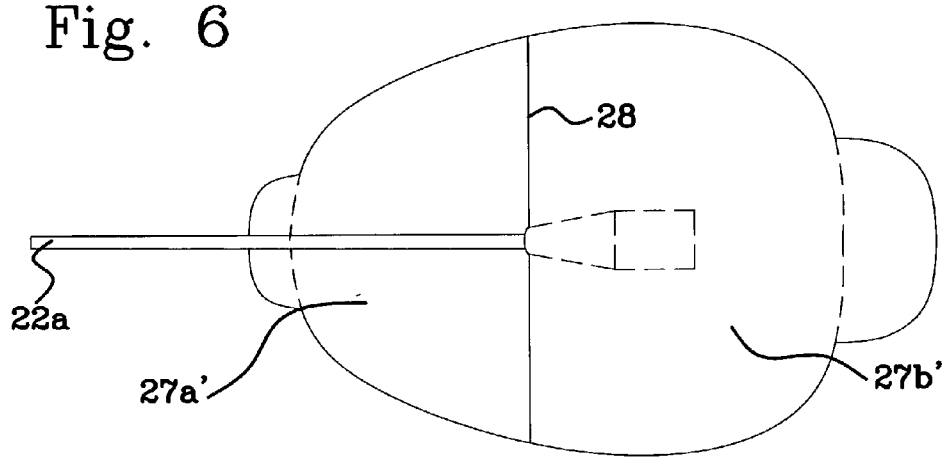
FIG. 6 is a bottom view of the device of FIG. 5.

Preferably, and as seen particularly in FIG. 6, the protective sheet 27' is divided into two parts by a cut 28 extending perpendicularly to the axis of the catheter, i.e. parallel to the edge 24'. The cut is located along a line intersecting the point where the catheter protrudes from the lower surface 25b of the collar, or, more precisely, from the adhesive layer. Hereby, a forward portion 27a' of the sheet may be peeled off in a forward direction, starting from the cut, or in a backward direction, starting from the forward edge of the protective sheet. Likewise, a rear portion 27b' of the sheet may be peeled off in a backward direction, starting at the cut, or, in a forward direction, starting at the rear edge of the sheet.

Figure 5:
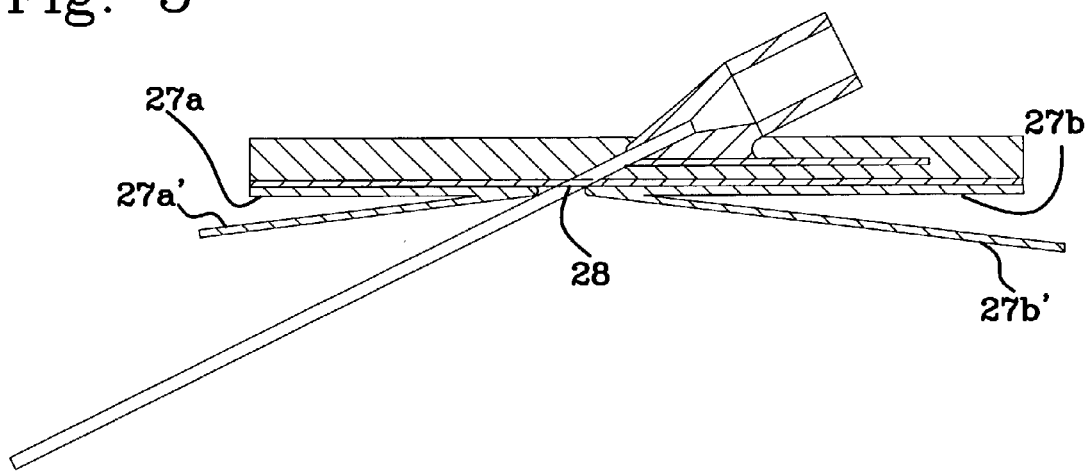
FIG. 5 is a similar cross section as FIG. 4, but showing a preferred arrangement of a protective sheet.

The peeling off of the protective sheet is facilitated if, according to FIGS. 5 and 6, instead of a cut 28, the two sheet portions 27a, 27b are extended and folded over on themselves so as to extended forwardly and backwardly, respectively, (see FIG. 5) providing free flaps 27a', 27b' that are easily gripped for peeling. These flaps are preferably protruding beyond the respective end edge of the collar as shown.

Figure 7:
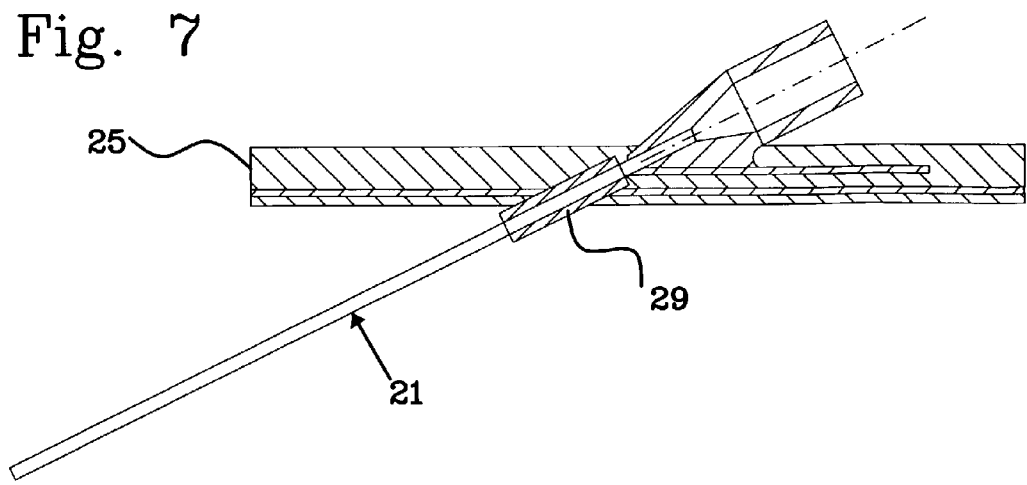
FIG. 7 is a cross section corresponding to FIG. 4 showing a further embodiment of the device.

FIG. 7 shows how a tube 29 of titanium is slipped over the catheter 21 and partly embedded in the material of the collar 25. A lower end of the tube extends into the insertion site. This is considered promoting tissue integration and avoiding contamination.

The invention being thus described, it will be obvious that the same may be varied in many ways. Such variations are not to be regarded as departure from the spirit and scope of the invention, and all such modifications as would be obvious to one skilled in the art were intended to be included within the scope of the following claims.

What is claimed is:

1. A transcutan catheter assembly including a collar of a relatively flexible material having an upper surface and a lower surface, the lower surface having adhesive properties, and a catheter extending in a fluid tight manner through the collar such that a distal end thereof protrudes underneath the lower surface of the collar and a proximal end thereof is accessible at the upper surface of the collar comprising:
   stabilization means at least partly embedded in the relatively flexible material for reinforcing the collar, said stabilization means including a first portion embedded in the relatively flexible material and a second portion protruding above the relatively flexible material and being adapted to receive the catheter.

2. The catheter assembly according to claim 1, wherein the first portion of the stabilization means at least partly has a net structure.

3. The catheter assembly according to claim 1, wherein the catheter and the collar are integrally formed.

4. The catheter assembly according to claim 1, wherein the relative flexible material is a hydrocolloid.

5. A transcutan catheter assembly comprising:
   a collar of a relatively flexible material having an upper surface and a lower surface, the lower surface having adhesive properties;
   a catheter extending in a fluid tight manner through the collar such that a distal end thereof protrudes underneath the lower surface of the collar and a proximal end thereof is accessible at the upper surface of the collar; and
   a reinforcement member at least partly embedded in the relatively flexible material for reinforcing the collar, said reinforcement member including a first portion embedded in the relatively flexible material and a second portion protruding above the relatively flexible material and being adapted to receive the catheter.

6. The catheter assembly according to claim 5, wherein the first portion of the reinforcement member at least partly has a net structure.

7. The catheter assembly according to claim 5, wherein the catheter and the collar are integrally formed.

8. The catheter assembly according to claim 5, wherein the relative flexible material is a hydrocolloid.

* * * * *